United States Patent
Pavlovic et al.

(10) Patent No.: US 8,631,953 B2
(45) Date of Patent: Jan. 21, 2014

(54) CLOSURE FOR CONTAINER FOR HOLDING BIOLOGICAL SAMPLES

(75) Inventors: Erin Kim Pavlovic, Zion, IL (US); Keith A. Haapala, Bristol, WI (US); Joseph F. Welk, Mt. Prospect, IL (US)

(73) Assignee: Abbott Laboratories, Abbott Park, IL (US)

( * ) Notice: Subject to any disclaimer, the term of this patent is extended or adjusted under 35 U.S.C. 154(b) by 1993 days.

(21) Appl. No.: 11/200,976

(22) Filed: Aug. 10, 2005

(65) Prior Publication Data

US 2007/0034592 A1 Feb. 15, 2007

(51) Int. Cl.
*B65D 51/00* (2006.01)
*A61B 19/00* (2006.01)

(52) U.S. Cl.
USPC .......... 215/249; 215/232; 215/247; 215/253; 220/359.3; 604/415

(58) Field of Classification Search
USPC .................. 215/232, 247, 249, 253; 220/229, 220/359.3; 604/415
See application file for complete search history.

(56) References Cited

U.S. PATENT DOCUMENTS

| | | | |
|---|---|---|---|
| 4,254,884 A | | 3/1981 | Maruyama |
| 4,652,429 A | * | 3/1987 | Konrad ................... 422/102 |
| 4,863,051 A | * | 9/1989 | Eibner et al. ............. 215/261 |
| 5,012,946 A | * | 5/1991 | McCarthy ............... 220/258.2 |
| 5,297,599 A | * | 3/1994 | Bucheli ................... 141/329 |
| 5,779,074 A | | 7/1998 | Burns |
| 5,819,964 A | * | 10/1998 | Grimard .................. 215/249 |
| 6,054,099 A | | 4/2000 | Levy |
| 6,723,289 B2 | | 4/2004 | Iheme et al. |
| 6,806,094 B2 | | 10/2004 | Anderson et al. |
| 2002/0113033 A1 | | 8/2002 | Claessens |
| 2002/0127147 A1 | | 9/2002 | Kacian et al. |
| 2002/0131902 A1 | | 9/2002 | Levy |
| 2004/0144474 A1 | | 7/2004 | Drummond et al. |
| 2005/0059161 A1 | | 3/2005 | Anderson et al. |
| 2005/0079633 A1 | | 4/2005 | Kacian et al. |

FOREIGN PATENT DOCUMENTS

| | | |
|---|---|---|
| EP | 1 435 254 A2 | 7/2004 |
| EP | 1 495 811 | 12/2005 |
| GB | 612 046 A | 11/1948 |
| WO | 02/072265 | 9/2002 |

OTHER PUBLICATIONS

'Hardness Measurement and Specifications.' http://www.machinist-materials.com/hardness.htm. Feb. 2010.*
Encyclopedia of Polymer Science and Engineering, $2^{nd}$ Edition, vol. 8, John Wiley & Sons, Inc. (1987), pp. 102-137.
The PCT Search Report Jan. 18, 2007.

* cited by examiner

*Primary Examiner* — Anthony Stashick
*Assistant Examiner* — James N Smalley
(74) *Attorney, Agent, or Firm* — Timothy P. Lucier

(57) ABSTRACT

A closure for a container, e.g., a tube, for a sample, e.g., a biological sample. The closure comprises a cap having a first opening and a second opening, the first opening capable of communicating with the mouth of a container, the second opening sealed by an exterior seal, and intermediate the first opening and the exterior seal, an interior seal. The invention also provides an assembly comprising the closure of this invention and a container. The invention also provides a method for preparing the closure.

30 Claims, 9 Drawing Sheets

CLOSURE FOR CONTAINER FOR HOLDING BIOLOGICAL SAMPLES

FIELD OF THE INVENTION

This invention relates to closures, and, more particularly, to closures for containers.

DISCUSSION OF THE ART

Capping and uncapping of containers, e.g., tubes containing biological samples, is a repetitive task that is performed daily in analytical laboratories. The task is difficult to automate. In addition, the task subjects analytical chemists to a considerable risk of exposure to biohazards. Furthermore, the task can also cause numerous injuries. Capping and uncapping of containers containing biological samples is also time-consuming. It has been estimated that the task requires about 0.6 minute per container or approximately 60 minutes per analytical batch at a cost of approximately $150 per batch. Indirect savings from preventing work-related injuries and improving the morale of analytical chemists cannot be estimated, but such savings may be substantial. For these reasons, analytical laboratories prefer that sample tubes be equipped with pierceable caps.

Sample tubes equipped with pierceable caps are available from several vendors. An example of a pierceable cap is described in United States Patent Application Publication No. 2002/0127147. This cap is claimed to be able to form an essentially leak-proof seal with an open-ended vessel capable of receiving and holding fluid specimens or other materials for analysis. The aforementioned publication describes a cap having a frangible seal that is penetrable by a plastic pipette tip or other fluid transfer device. The cap further includes filtering means for limiting dissemination of an aerosol or bubbles once the frangible seal has been pierced. The filtering means is positioned between the frangible seal and retaining means. The retaining means is positioned on the cap above the filtering means and may be used to contain the filtering means within the cap. The retaining means is made of a material that is penetrable by a fluid transfer device. Commercially available caps have been made of elastic material designed to form a tight seal around a sampling device, e.g., a pipette or a needle. The junction between the sampling device and the septum is usually gas-tight. Withdrawal of liquid can often create a substantial vacuum that will interfere with the action of sampling. In addition, the sample tube may have to be held down by force, because the residue of the pierced cap may bind with the sampling device as the sampling device is withdrawn from the sample tube. In addition, puncturing the seal of the cap with a blunt or thick object, such as the tip of a pipette, may damage the tip of the pipette.

Accordingly, it would be desirable to provide a closure for a container that eliminates the need for capping and uncapping the container. It would also be desirable to provide a closure for a container that does not interfere with the sampling activity of the sampling device. It would also be desirable to provide a closure for a container that can be opened by a sampling device, without leading to damage of the sampling device. It would also be desirable to provide a closure that can be opened without adversely affecting the sample itself.

Further desirable features include a sample tube that would enable convenient collection of the sample at the customer's site, a sample tube that can be used for either specimens collected via swabs or urine specimens, a sample tube that can be directly loaded on the sample preparation portion of an analytical instrument, a sample tube that would not have to be opened by laboratory technicians before the sample tube is ready for the sample preparation portion of an analytical instrument, a sample tube that would withstand shipping stresses, a sample tube for swabs that would not require removal of the swab before the sample tube is ready for the sample preparation portion of an analytical instrument, a sample tube that would facilitate identification of the sample for processing, and a sample tube that would eliminate the need for rapid transportation and processing of the specimen.

SUMMARY OF THE INVENTION

In one aspect, this invention provides a closure for a container, e.g., a tube, for a sample, e.g., a biological sample. The closure comprises a cap having a first opening and a second opening, the first opening capable of communicating with the mouth of a container, the second opening having an exterior seal, e.g., a polymeric cover, and intermediate the first opening and the exterior seal, an interior seal, e.g., a rupturable membrane. In a second aspect, this invention provides an assembly comprising the closure of this invention and a container. In a third aspect, this invention provides a method for preparing the closure.

In one embodiment of the closure of this invention, the cap is typically substantially cylindrical in shape and is characterized by having a circular top with a substantially cylindrical sidewall descending from the top. The first opening and the second opening generally surround the major axis of the substantially cylindrically-shaped cap. The openings have dimensions of a size sufficient to accommodate a sampling device for obtaining access to the contents of the container. The cap is typically made of a resilient polymeric material. The exterior seal is typically made of an elastomeric material. The interior seal is typically made of a laminate comprising at least one layer of metallic foil and preferably a layer of a heat sealable adhesive, and, optionally, a layer of paper.

The sample tube typically has a minimum fill volume of 1.2 milliliters. It is preferred that the sealed sample tube pass a leak qualification test. The sample tube can be fitted into a sample rack, and the contents thereof can be aspirated by the disposable tip of a pipette. The length of the sample tube typically does not exceed 95 mm. The outside diameter of the sample tube typically does not exceed 18 mm. The sample tube is typically made of a polymeric material, preferably a resilient polymeric material, e.g., polypropylene. The volume of fill without overflow due to displacement of the tip of a pipette is typically about eight milliliters; the volume displaced by the tip of a pipette is typically about one milliliter.

A pipette can be used as the sampling device to provide access to the sample through the second opening in the closure and the first opening in the closure. The structure of the closure ensures that a vacuum will not be created. When the tip of the pipette breaks the exterior seal of the closure and the interior seal of the closure, the pipette and the tip thereof will not be damaged.

The closure of this invention provides numerous benefits. One major benefit is the facilitation of automation of sampling operations. A second major benefit is the reduction of exposure of analytical chemists to biohazardous materials. A third major benefit is the saving of time in obtaining access to the contents of a container, which also results in a reduction of costs associated with obtaining access to the contents of the container. A fourth major benefit is the allowing of a sampling device to open the closure without the sampling device being damaged by the opening process. A fifth major benefit is the ability to open the closure without adversely affecting the sample itself. A sixth major benefit is that the closure does not interfere with the sampling activity of the sampling device.

The closure of this invention can be prepared by a method in which an apparatus having a molding unit comprising (1) at least one cavity half and at least one core half, the at least one cavity half comprising a cavity, and the at least one core half comprising a mold core, (2) a punch, and (3) a die is provided. In addition, a web comprising a material for preparing the interior seal of the closure is provided. In the first step of the method, a portion of the web is indexed to the molding unit, so that the punch and the die are aligned with the portion of the web in the molding unit. Then, the molding unit is closed, thereby enabling the punch and the die to cut the material of the web for forming the interior seal of the closure. The cut material of the web is maintained on the mold core until the termination of a first molding cycle. During the first molding cycle, polymeric material for forming the cap portion of the closure is introduced into the closed molding unit, so as to allow the cut material of the web to adhere to the polymeric material introduced into the closed molding unit. At the termination of the first molding cycle, the molding unit is opened, while the assembly of the cap portion of the closure and the interior seal of the closure remain on the mold core. The mold core is then positioned so as to enable introduction of polymeric material into the molding unit to form the exterior seal of the closure in a second molding cycle. The molding unit is then closed, whereupon polymeric material for forming the exterior seal of the closure is introduced into the closed molding unit during the second molding cycle. Finally, at the termination of the second molding cycle, the molding unit is opened and the finished closure is removed from the mold core.

BRIEF DESCRIPTION OF THE DRAWINGS

FIG. 10A is a front view in elevation of an apparatus that can be used to make the closure of this invention. FIG. 10B is a plan view of a portion of the apparatus that can be used to make the closure of this invention. FIG. 10C is a side view in elevation of the apparatus that can be used to make the closure of this invention, in which view the apparatus is being prepared to carry out the step of the method for forming the interior seal of the closure. FIG. 10D is a side view in elevation of the apparatus that can be used to make the closure of this invention, in which view the punch and the die plate are forming the interior seal of the closure, and polymeric material is being introduced into the molding unit to form the cap of the closure. FIG. 10E is a side view in elevation of the apparatus that can be used to make the closure of this invention, in which view the punch is being retracted, and the unfinished closure remains on the mold core. FIG. 10F is a side view in elevation of the apparatus that can be used to make the closure of this invention, in which view polymeric material for forming the exterior seal of the closure is introduced into the molding unit. FIG. 10G is a side view in elevation of the apparatus that can be used to make the closure of this invention, in which view the molding unit is opened and the finished closure is removed from the molding unit.

DETAILED DESCRIPTION

Figures 1, 2:
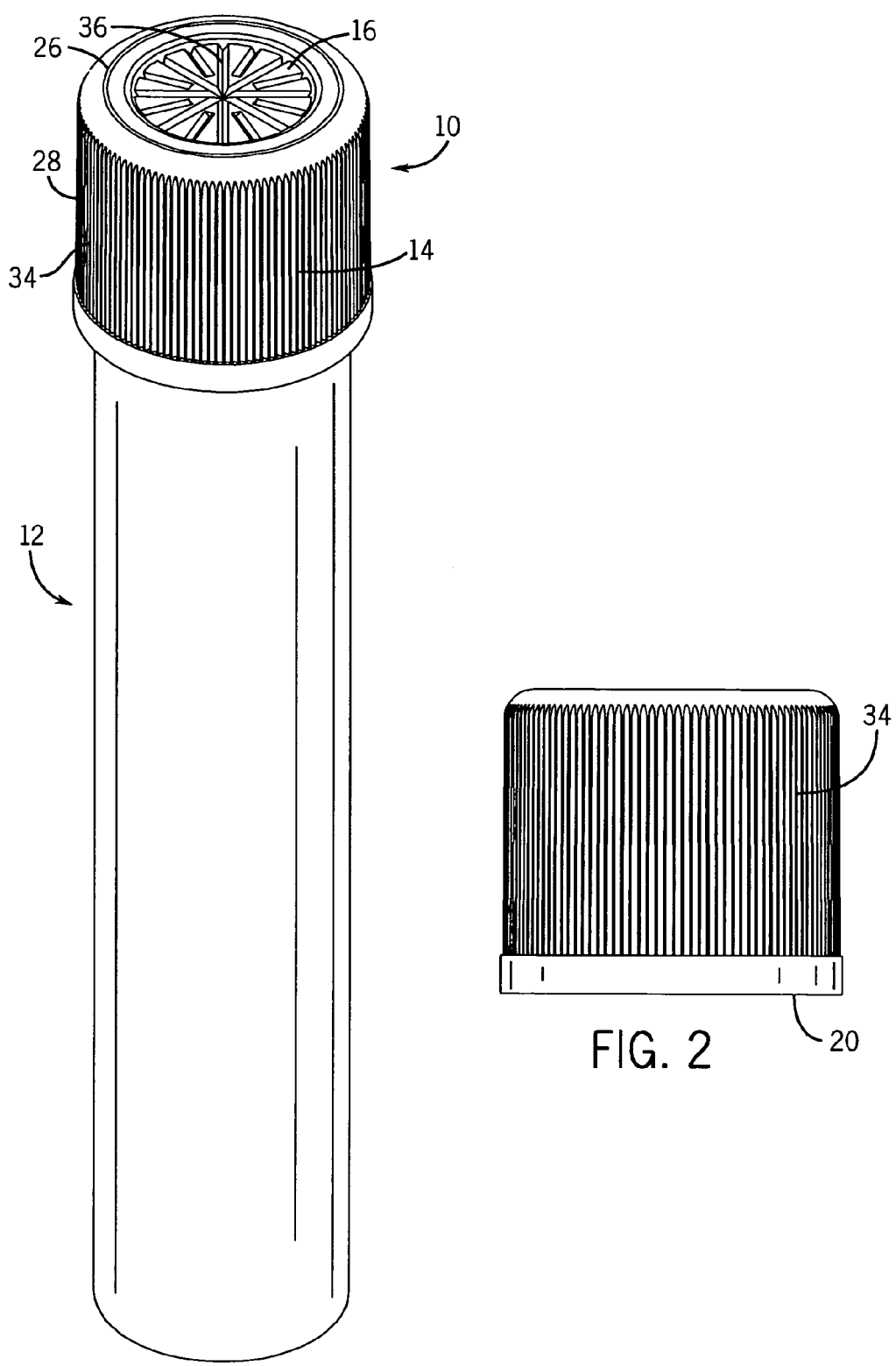
FIG. 1 is a perspective view of one embodiment of the closure of this invention attached to a container, e.g., a sampling tube.
FIG. 2 is a side view in elevation of the closure of FIG. 1, not attached to a container.

As used herein, the term "closure" means an article that closes and seals a container, e.g., a sample tube. The term "cap" means the portion of a closure that is attached to the container. In one embodiment of the closure of this invention, the cap has threads formed in the interior wall thereof to enable the cap to be screwed onto the container. In other embodiments, the cap can be attached to the container by a friction fit, a snap fit, or some other type of fit. The phrase "exterior seal" means the portion of the closure that seals the container and, when the container is closed, has one major surface thereof facing the environment external to the container. The phrase "interior seal" means the portion of the closure that seals the container and, when the container is closed, is disposed completely within the volume formed by the closure and the container. The phrase "rupturable membrane" means a membrane comprising at least one layer of a brittle material, e.g., a metallic foil, which membrane can be ruptured by the tip of a pipette. The rupturable membrane typically further comprises at least one layer of heat sealable adhesive, and, optionally, at least one layer of paper. The expression "sampling device" means a device for removing a sample of liquid from a container. The term "pierceable" means capable of being punctured by the tip of a pipette without adversely affecting the tip.

This invention provides a closure for a container for biological samples. Referring now to FIGS. 1, 2, 3, 4, 5, 6, and 7, a closure 10 for a container 12 comprises a cap 14, an exterior seal 16 for the cap 14, and an interior seal 18. The cap 14 has a first opening 20 and a second opening 22. The first opening 20 is capable of communicating with the mouth (not shown) of the container 12. The second opening 22 allows initial access of a sampling device, e.g., the tip of a pipette, to the container 12.

In the embodiment shown in FIGS. 1, 2, 3, 4, 5, 6, and 7, the cap 14 is a structure having a substantially cylindrical shape comprising a circular top 26 and having a substantially cylindrically-shaped wall 28 depending from the periphery of the top 26. In the embodiment shown in FIGS. 1, 2, 3, 4, 5, 6, and 7, the interior surface 30 of the substantially cylindrically-shaped wall 28 of the cap 14, i.e., the surface facing the mouth of the container 12, comprises threads 32. By means of these threads 32, the cap 14 can be screwed onto the threaded neck of a container. The interior surface 30 of the substantially cylindrically-shaped wall 28 of the cap 14 is not required to contain threads. For example, in another embodiment, the substantially cylindrically-shaped wall 28 of the cap 14 can be constructed to fit over the neck of a container by means of friction only. Alternatively, in still another embodiment, the substantially cylindrically-shaped wall 28 of the cap 14 can be constructed to fit over the neck of a container by means of a snap-fit ring. It should be noted that the cap 14 need not be substantially cylindrical in shape. In other words, the particular shape of the cap 14 is not critical. However, the cap 14 must be of such a shape and construction that it can fit over the mouth of the container 12 and maintain the closure 10 in the proper position. As shown in FIGS. 1 and 2, the exterior surface 34 of the substantially cylindrically-shaped wall 28 of the cap 14 is characterized by a pattern of ridges. However, the exterior surface 34 of the substantially cylindrically-shaped wall 28 of the cap 14 can have no pattern or can have another pattern, if so desired.

The cap 14 is made of a polymeric material, preferably polypropylene. The polymeric material is compatible with DNA and/or RNA. Alternative polymeric materials for polypropylene include, but are not limited to, polyethylene, polyvinyl chloride, and other polymeric material that is compatible with DNA and/or RNA. It is further preferred that polymeric material forming the cap 14 be a resilient polymeric material, for the reason that a resilient polymeric material can withstand the shock of being dropped onto a floor. A suitable polymeric material for preparing the cap 14 is Basell "Pro-fax" grade 6323 polypropylene homopolymer resin mixed with a colorant, e.g., an orange colorant (PolyOne CC10056423WE at a resin:colorant ratio of 25:1). According to the product information sheet for Basell "Pro-fax" grade 6323, the polymer is a general purpose polypropylene homopolymer resin. The resin has a UL yellow card RTI of 110° C. to a minimum thickness of 0.040 inches and a flame rating of UL94HB to a minimum thickness of 0.058 inches. These ratings apply only to a natural color resin. The density-specific gravity is 0.900 sp gr 23/23° C. (Method B) ASTM D 792, a melt flow rate of 12.0 g/10 min (230° C./2.16 kg), a tensile strength at yield of 33.8 MPa (50 mm/min) ASTM D 638, a tensile strength at yield of 4900 psi (2 in/min), a flexural modulus of 1450 MPa (1 mm/min) ASTM D 790, a flexural modulus of 210000 psi (0.05 in/min), a tensile elongation at yield of 10% ASTM D 638, a notched Izod impact of 37.4 J/m (23° C.), a notched Izod impact of 0.700 ft-lb/in (73° F.) ASTM D 256, a Rockwell hardness of 88 (R-Scale), and a DTUL at 66 psi—Unannealed of 92.2° C. ASTM D648.

Figure 3:
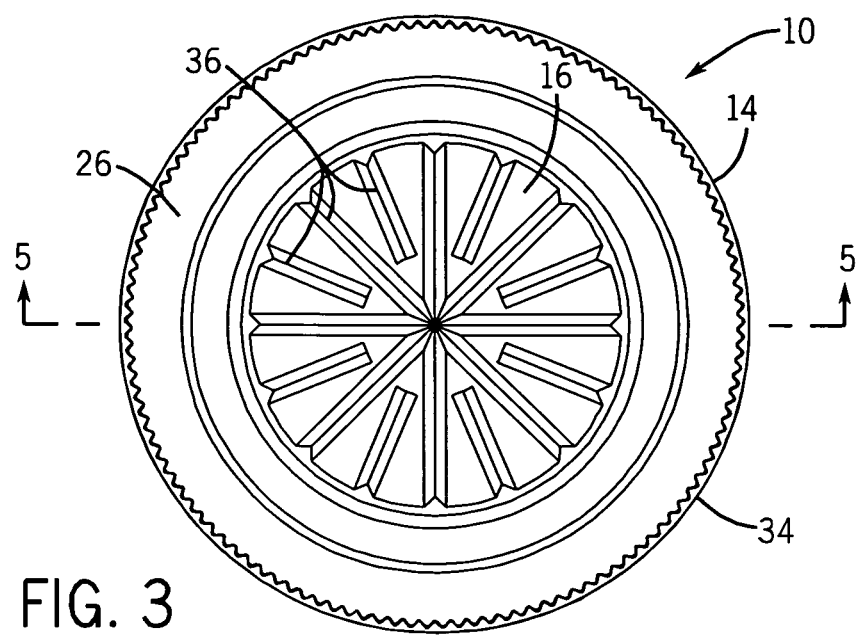
FIG. 3 is a top plan view of the embodiment of the closure of FIG. 2.
Figure 4:
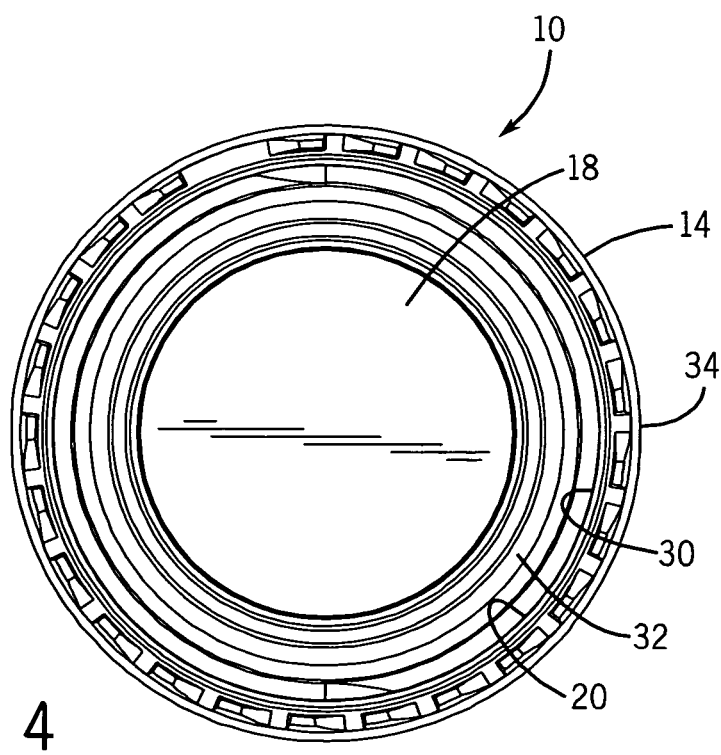
FIG. 4 is a bottom plan view of the embodiment of the closure of FIG. 2.
Figure 8:
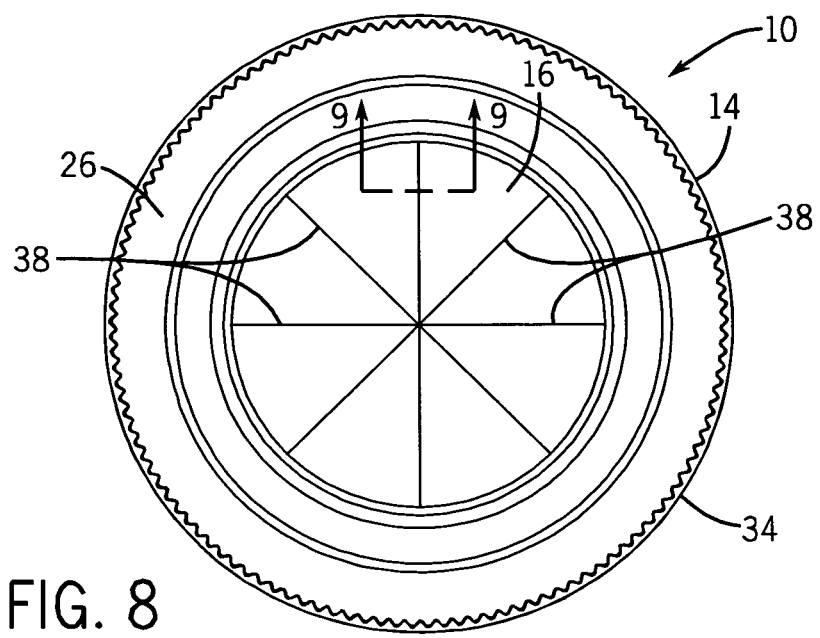
FIG. 8 is a top plan view of another embodiment of the closure of this invention.
Figure 9:
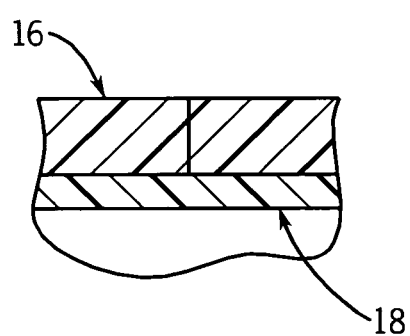
FIG. 9 is a cross-sectional view of the closure of FIG. 8, taken along line 9-9.

The second opening 22 of the cap 14 is sealed by means of the exterior seal 16. The exterior seal 16 is made of a polymeric material, preferably an elastomeric material, to impart strength to the seal. The exterior seal 16 can have at least one score line 36, typically a plurality of score lines 36 to facilitate piercing of the exterior seal 16 by means of the tip of a pipette. The score line 36 or score lines 36 also function to reduce the likelihood of a vacuum forming upon puncturing of the exterior seal 16. As shown in FIGS. 1 and 3, the score lines 36 extend radially from the center of the exterior seal 16. However, other patterns of score lines, such as, for example, a single circle or a plurality of concentric circles, straight parallel lines, zigzags, alphanumeric characters, dots, other repeating patterns, irregular patterns (i.e., no pattern, random score marks), can also be employed. In an alternative embodiment, as shown in FIGS. 8 and 9, the exterior seal 16 can have at least one slit 38 that passes through the entire thickness of the exterior seal 16 to expose the interior seal 18. Typically, only a single slit need be employed, but a plurality of slits is also acceptable. The geometry of the slit can be a single line or a plurality of lines. Furthermore, slits having geometrical shapes, e.g., a cross, a star, or patterns similar to those employed for the at least one score line, can be employed.

An elastomeric material for the exterior seal 16 typically has a hardness ranging from about 30 Shore A to about 90 Shore A, preferably 50 Shore A to about 80 Shore A. A representative example of a commercial embodiment of the exterior seal 16 has a hardness of 60 Shore A. An elastomeric material suitable for use in preparing the exterior seal 16 is a saturated styrenic elastomer, which is applied over the interior seal 18 to impart strength to the inner seal 18. An elastomeric material for an exterior seal suitable for use in this invention has the designation RTP Reference Number—RTP SX109669 Elastomer. The elastomeric material can be formulated by and obtained from RTP Company, 580 East Front Street, Winona, Minn. 55987 USA.

The exterior seal 16 can be made of a flexible material that retains some flexibility at temperatures of ranging from about +70° C. to about −70° C., the typical temperature for storing samples. Suitable materials for preparing the exterior seal 16 include, but are not limited to, natural rubber (retains flexibility down to a temperature of about −60° C.); styrene-butadiene rubber (retains flexibility down to a temperature of about −50° C.); polyisoprene (retains flexibility down to a temperature of about −55° C.); silicone rubber (retains flexibility down to a temperature of about −80° C.); fluorosilicone rubber (retains flexibility down to a temperature of about −60° C.); ethylene propylene rubber (retains flexibility down to a temperature of about −60° C.).

Between the first opening 20 and the second opening 22 of the cap 14 is an interior seal 18. The interior seal 18 is shown as being between the threads 32 on the interior surface 30 of the substantially cylindrically-shaped wall 28 of the cap 14 and the exterior seal 16. The purpose of the interior seal 18 is to prevent biological samples from being lost or otherwise adversely affected during transport. Because the sample is normally transported from a clinical site, the container, typically a tube, may assume any possible orientation during shipping (vertical, horizontal, inverted, etc.). Moreover, the container may experience changes in altitude, including changes of a magnitude sufficient to induce a pressure differential. The interior seal 18 is preferably non-stretching. The interior seal 18 can compensate for the potential failure of the exterior seal 16 (e.g., the potential failure of the exterior seal 16 to prevent a liquid from leaking or seeping from an inverted tube or partially inverted tube, and the like). Similarly, the exterior seal 16 can compensate for the potential failure of the interior seal 18 (e.g., the potential failure of the interior seal 18 to prevent a liquid from leaking or seeping from an inverted tube or partially inverted tube, and the like).

The interior seal 18 is made of such a material that it can be ruptured easily by means of the tip of a sampling device, e.g., a pipette. Suitable materials for forming the interior seal 18 include, but are not limited to, thin brittle materials, such as, for example, thin metallic foils (e.g., aluminum foil) and thin polymeric sheets (e.g., saturated styrenic elastomer). The particular thickness of the interior seal 18 can be selected by one having ordinary skill in the art. In addition to substantially eliminating evaporation and leakage, the interior seal 18 also provides evidence of physical integrity of the sample prior to analysis. The interior seal 18 can be in contact with the exterior seal 16. According to a desirable method for preparing the closure 10, the interior seal 18 will be in contact with the exterior seal 16.

The interior seal 18 can be a single layer of metallic foil or other brittle material, but is generally a composite material having a plurality of layers. In one multiple-layer embodiment, the interior seal 18 comprises a layer of metallic foil bearing a layer of heat sealable adhesive. In this embodiment, the exposed major surface of the layer of heat sealable adhesive faces the portion of the container that will contain the sample and the exposed major surface of the layer of metallic foil faces the exterior seal 16. In another multiple-layer embodiment, the interior seal 18 comprises a layer of metallic foil bearing a layer of heat sealable adhesive on one major surface thereof and a layer of paper on the other major surface thereof. The exposed major surface of the layer of heat sealable adhesive faces the portion of the container that will contain the sample and the exposed major surface of the layer of paper faces the exterior seal 16. A layer of adhesive can be used to adhere the layer of paper to the layer of foil. In one multiple-layer embodiment containing four layers, the interior seal 18 comprises, from top to bottom, a layer of paper 18a (having a weight per area of from about 25 g/m² to about 75 g/m², preferably from about 37.6 g/m² to about 42.4 g/m²), a layer of adhesive lacquer 18b (having a weight per area of from about 2.0 g/m² to about 3.0 g/m²), a layer of metallic foil 18c, e.g., aluminum foil (having a thickness ranging from about 5 μm to about 70 μm, preferably from about 33.7 μm to about 40.3 μm) (a weight per area of from about 91.0 g/m² to about 108.8 g/m²), and a layer of a heat sealable adhesive 18d (having a weight per area of from about 2.0 g/m² to about 8.0 g/m², preferably from about 3.0 g/m² to about 4.0 g/m²). The layer of paper 18a of the interior seal 18 is in contact with the exterior seal 16. The interior seal 18 can be obtained commercially from HUECK FOLIEN GmbH & Co. KG, Pirkmühle, 92712 Pirk, Germany (Reference number 6116324—Pap40 Kraft paper overlying a layer of adhesive lacquer, which, in turn, overlies a layer of soft temper aluminum foil (37 μm thick), which, in turn, overlies a layer of heat sealable adhesive, designated as LPP2). The foil layer can be thinner or thicker than 37 μm; the foil layer can be made of a metal other than aluminum; the foil layer can be made of a liquid impervious, brittle material other than metal. The paper can have a specification ranging from about 25 g/m² to about 75 g/m², typically about 40 g/m². As indicated previously, a layer of paper is not required. Types of paper other than Kraft paper can be used. In place of paper, other brittle material can be used, e.g., brittle polymeric material. A layer of paper is generally used to increase the strength of the interior seal 18 with respect to drop force. The layer of paper also increases the brittleness of the interior seal 18 to improve the tearability of the interior seal 18. Furthermore, the layer of paper aids in reducing, preferably eliminating, the vacuum that can sometimes be observed when a portion of the interior seal 18 clings to a sampling device, e.g., the tip of a pipette. The interior seal 18 can be designed to have varying thickness over its major surfaces, such that only that portion of the interior seal 18 in register with the tip of a pipette is easily rupturable.

Because the interior seal 18 is made of a material that does not stretch easily, the advancing tip of the sampling device is capable of rupturing the interior seal 18. After being ruptured, the interior seal 18 will continue to be held in position by the cap 14. Alternatively, the interior seal 18 can be constructed so that it is able to fall into the container after being ruptured. The cap 14 can contain a shoulder, e.g., a circular shoulder in the case of a substantially cylindrically-shaped cap 14, to aid in holding the interior seal 18 in place.

Figure 5:
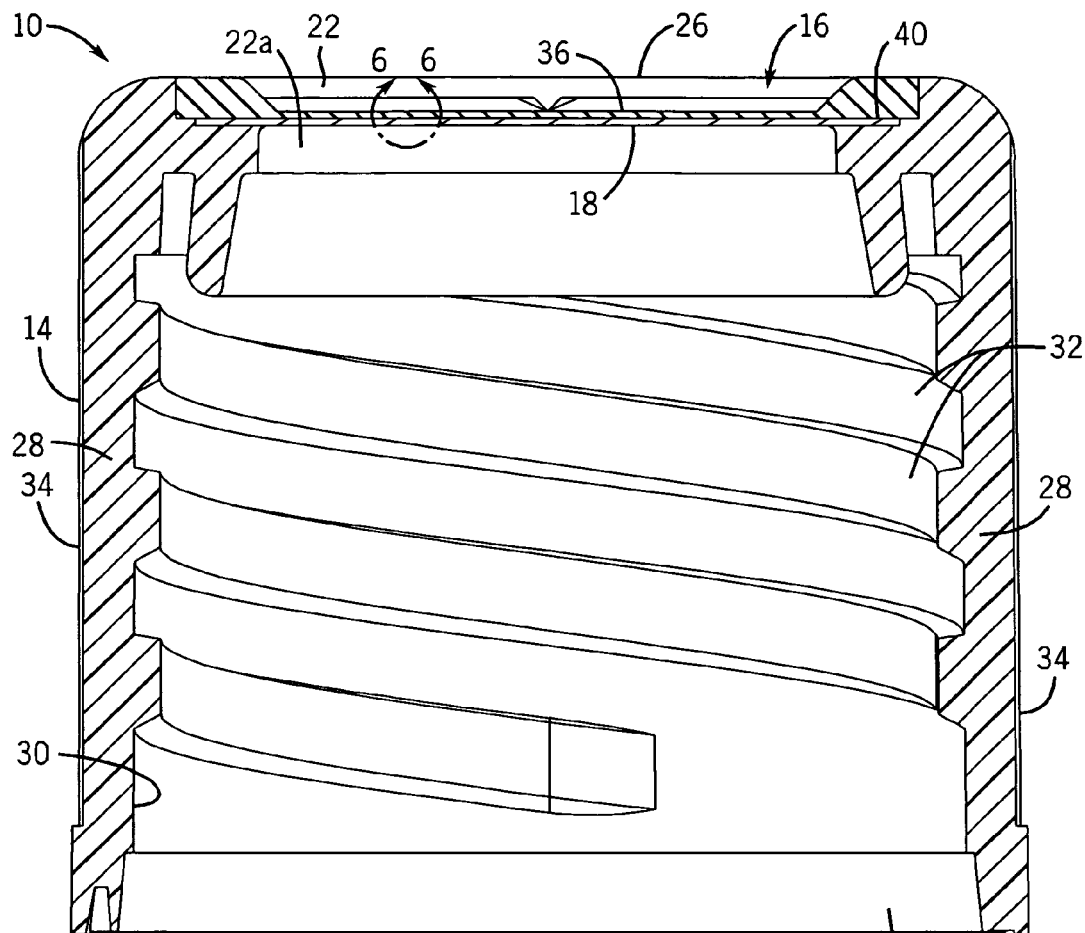
FIG. 5 is a cross-sectional view of the closure of FIGS. 2-4, taken along line 5-5.
Figure 6:
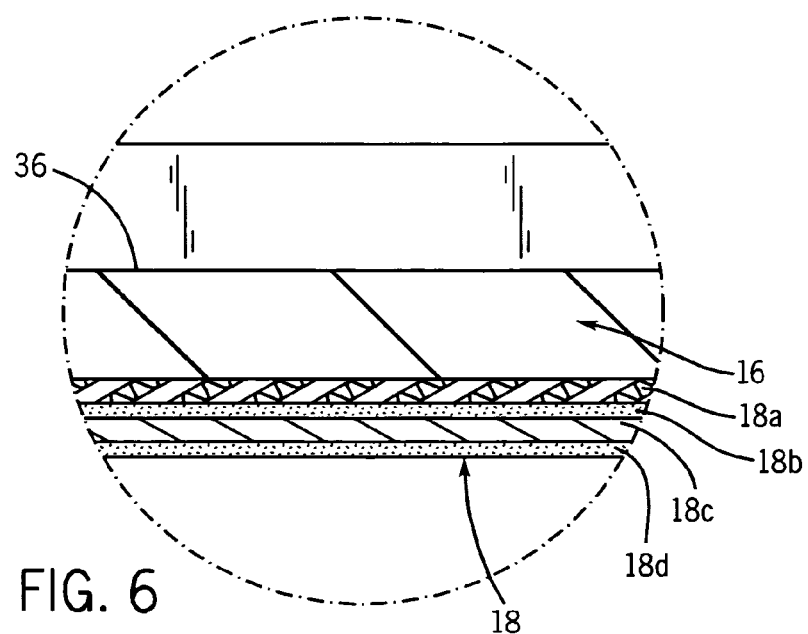
FIG. 6 is an enlarged view of a portion of the closure of FIG. 5, taken along line 6-6.
Figure 7:
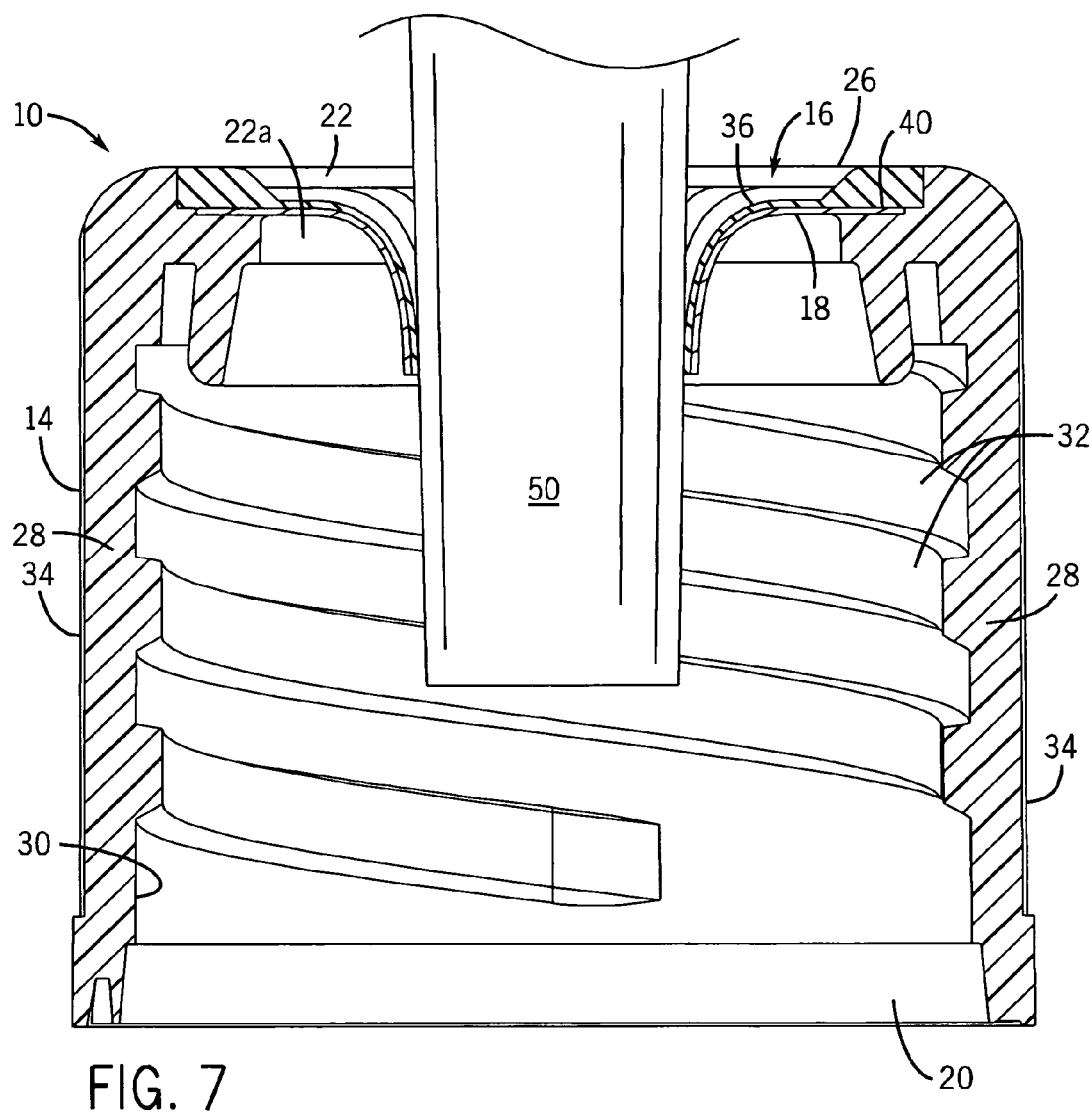
FIG. 7 is a view of the closure of FIG. 5, illustrating a sampling device, e.g., the tip of a pipette, inserted into the second opening of the closure of FIG. 5.

Referring now to FIGS. 5 and 7, the closure 10 in FIG. 5 is shown as being closed, with no sampling device entering through the second opening 22. The closure 10 in FIG. 7 is shown with a sampling device 50, e.g., the tip of a pipette, positioned through the second opening 22. The openings 20 and 22 of the closure 10 allow the sampling device 50 to easily pass through the closure 10 to obtain access to the contents of the container 12; the openings 20 and 22 of the closure 10 also allow the sampling device 50 to be easily withdrawn from the closure 10.

While the dimensions of the components of the closure of this invention are not critical, typical dimensions are being provided to illustrate the size of a typical closure. For use with a substantially cylindrical sample tube having a nominal outside diameter of about 16 mm, a cylindrical cap 14 can have a nominal outside diameter of about 17 mm, a nominal inside diameter of about 16 mm, and a wall thickness of about ½ mm (thickness is equal to approximately one-half the difference between the outside diameter and the inside diameter). Regardless of the nominal inside diameter of the closure 10 and the nominal outside diameter of the sample tube 12, the closure 10 and the sample tube 12 should have dimensions such that when the sample tube 12 is closed by the closure 10, leakage of the sample from the sample tube 12 is not excessive for the purpose intended. The nominal height of the sidewall 34 of the cap 14 is about 15 mm. A sampling device that can be used with the foregoing cap 14 can have a diameter of approximately 3.9 mm.

While the dimensions of a sample tube 12 suitable for use with the closure of this invention are not critical, typical dimensions are being provided to illustrate the specifications of a typical sample tube. The sample tube 12 typically has a minimum fill volume of 1.2 milliliters. The sealed sample tube must pass a leak qualification test, the criteria of which can be based on ASTM Designation D 5094—90 (Reapproved 1997), incorporated herein by reference. The sample tube 12 is typically capable of receiving a sample swab after the swab is broken. The sample tube 12 is capable of fitting into a sample rack and is capable of receiving pipette tips. The neck of the sample tube 12 must be compatible with the closure 10 when the sample tube 12 is closed by the closure 10 so that leakage of the sample from the sample tube 12 is not excessive for the purpose intended. For this reason, the sample tube 12 is typically made of a resilient polymeric material. The sample tube 12 is typically of sufficient length to accommodate a standard vertical barcode label, which may be about two inches in length. The sample tube 12 typically has a fill mark to indicate the fill point for a sample of urine. The length of the sample tube 12 preferably does not exceed 95 mm. The nominal outside diameter of the sample tube 12 preferably does not exceed 18 mm. The sample tube 12 is preferably made of a polymeric material, preferably a resilient polymeric material, e.g., polypropylene. The sample tube 12 is preferably translucent. A representative example of the nominal dimensions of a sample tube are 85 mm in length×16 mm outside diameter×15 mm inside diameter. Regardless of the dimensions of the sample tube 12, the closure 10 and the sample tube 12 should have dimensions such that when the sample tube 12 is closed by the closure 10, leakage of the sample from the sample tube 12 is not excessive for the purpose intended. The volume of the sample tube to the rim is typically 10 mL. The volume of fill without overflow due to displacement of the tip of a pipette is typically eight milliliters; the tip of the pipette typically displaces about one milliliter of the sample.

The shape of the sample tube 12 and the shape of the closure 10 are not critical. While the sample tube 12 is shown as being cylindrical and having a circular mouth, the sample tube 12 can have a mouth that circumscribes a polygon, such as, for example, a rectangle, a hexagon, an octagon, or the like. If the sample tube 12 is cylindrical and has a circular mouth, it is preferred that the opening 20 of the closure 10 be circular. If the mouth of the sample tube 12 is not circular, the opening 20 of the closure 10 should have a shape that is compatible with, and preferably matching to, the shape of the mouth of the sample tube 12. The shape of the container 12 is not critical. The container 12 need not be tubular in shape, but can be of any shape common to containers typically found in a laboratory that handles biological samples. In the case of a substantially cylindrical sample tube, the bottom can be rounded, as shown in FIG. 1. In an alternative embodiment (not shown), the bottom of the sample tube can be conically-shaped, or can even be of some other shape.

The cap 14 can be prepared by means of a molding process, typically an injection molding process. See, for example, *Encyclopedia of Polymer Science and Engineering*, 2nd Edition, Vol. 8, John Wiley & Sons, Inc. (1987), pages 102-137, incorporated herein by reference.

The interior seal 18 can be adhered to the cap 14 by means of a molding process, typically an injection molding process. See, for example, *Encyclopedia of Polymer Science and Engineering*, 2nd Edition, Vol. 8, John Wiley & Sons, Inc. (1987), pages 102-137, previously incorporated herein by reference. The major surfaces of the interior seal 18 are of a shape to conform to the shape of the container 12, the cap 14, and the exterior seal 16. The areas of the major surfaces of the interior seal 18 can be greater than the area of an opening 22a of the cap 14 that is disposed between the interior seal 18 and the opening 20 of the cap 14. When the area of the interior seal 18 exceeds the area of the opening 22a of the cap 14, the interior seal 18 is preferably adhered to the cap 14 by way of a shoulder 40 of the cap 14. The shoulder 40 of the cap 14 surrounds the opening 22a of the cap 14. The peripheral edge of the interior seal 18 then adheres to the shoulder 40 of the cap 14.

The exterior seal 16 can be formed by means of a molding process, typically an injection molding process. See, for example, *Encyclopedia of Polymer Science and Engineering*, 2nd Edition, Vol. 8, John Wiley & Sons, Inc. (1987), pages 102-137, previously incorporated herein by reference.

When the interior seal 18 is adhered to the cap 14 in the manner described below, a major surface of the exterior seal 16 and a major surface of the interior seal 18 will be in contact. It is also possible to position the interior seal 18 in the cap 14 so that no major surface of the exterior seal 16 is in contact with any major surface of the interior seal 18. Such a manner of positioning can be carried out by one of ordinary skill in the art without undue experimentation.

Figure 10B:
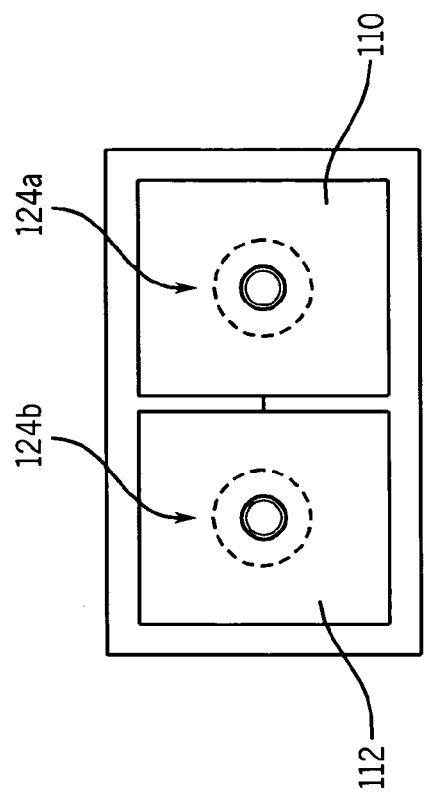
FIGS. 10A through 10G are a series of schematic diagrams illustrating a method suitable for making the closure of this invention.
Figure 10A:
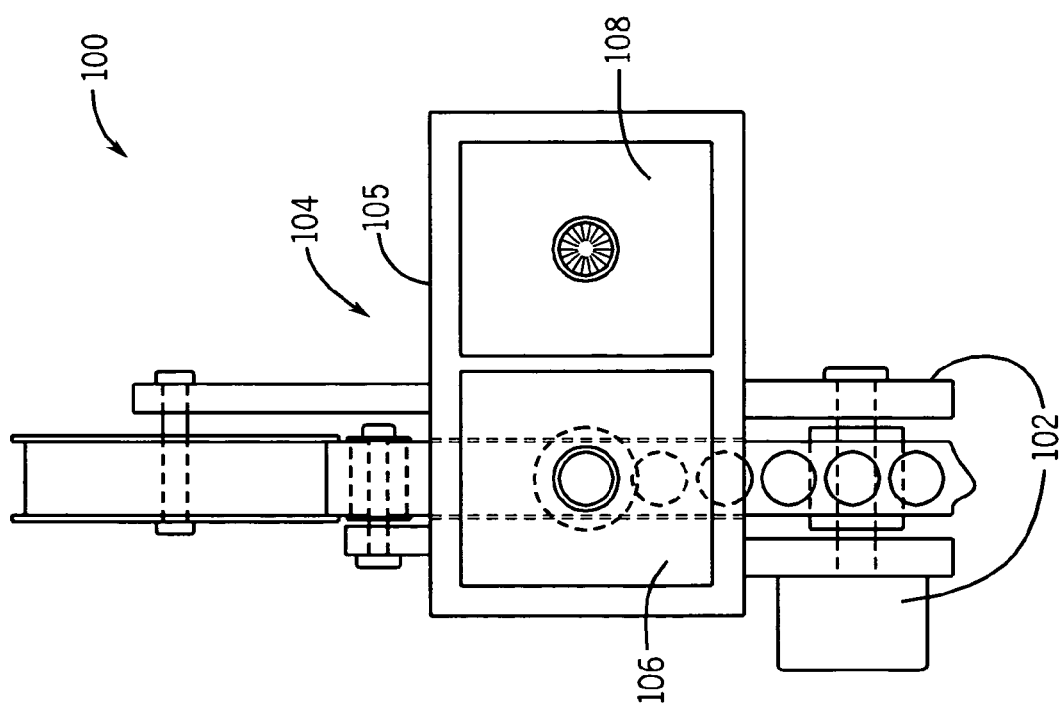

Turning now to FIGS. 10A through 10G, inclusive, FIG. 10A illustrates a front view in elevation of one system for preparing the closure 10 of this invention. The system 100 comprises a mechanism 102 for feeding a web comprising material for forming the interior seal 18 to a mold zone 104 of the system 100. The mold zone 104 comprises a molding unit 105 having first cavity half 106 for receiving the web and the polymeric material for forming the cap 14 of the closure 10. The molding unit 105 also comprises a second cavity half 108 for receiving the polymeric material for forming the exterior seal 16 of the closure 10. Referring to FIG. 10B, the molding unit 105 further comprises a first core half 110 for forming the cap 14 and the interior seal 18 of the closure 10 and a second core half 112 for forming the exterior seal 16 on the cap 14 of the closure 10. The first core half 110 and the second core half 112 are capable of being switched, such as, for example, by rotation, to carry out a two-shot molding process. In other words, the first core half 110 can be used with the first cavity half 106 in a first molding step and can then be switched, whereby the first core half 110 can be used with the second cavity half 108 in a second molding step. When the first core half 110 is being used with the second cavity half 108 to complete a given closure, the second core half 112 can be used with the first cavity half 106 in a first molding step to begin another closure. One of ordinary skill in the art can readily observe how switching the first core half 110 and the second core half 112 between the first cavity half 106 and the second cavity half 108 can increase throughput of production of closures. Furthermore, the system can be scaled up via additional molding units to produce an even higher quantity of closures. While not shown in FIGS. 10A and 10B, when the molding unit 105 is closed, one of the core halves 110 or 112 is in register with one of the cavity halves 106 or 108, and the other of the core halves 110 or 112 is in register with the other of the cavity halves 106 or 108. The other parts of the molding unit 105 are well known to one of ordinary skill in the art and are described, for example, in *Encyclopedia of Polymer Science and Engineering*, 2nd Edition, Vol. 8, John Wiley & Sons, Inc. (1987), pages 102-137, previously incorporated herein by reference.

Figure 10D:
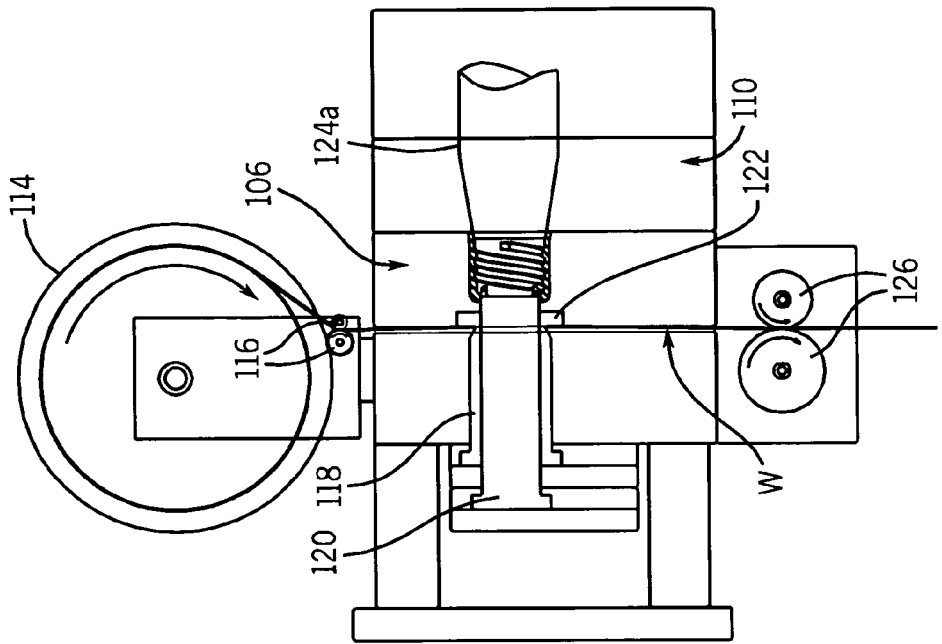
Figure 10C:
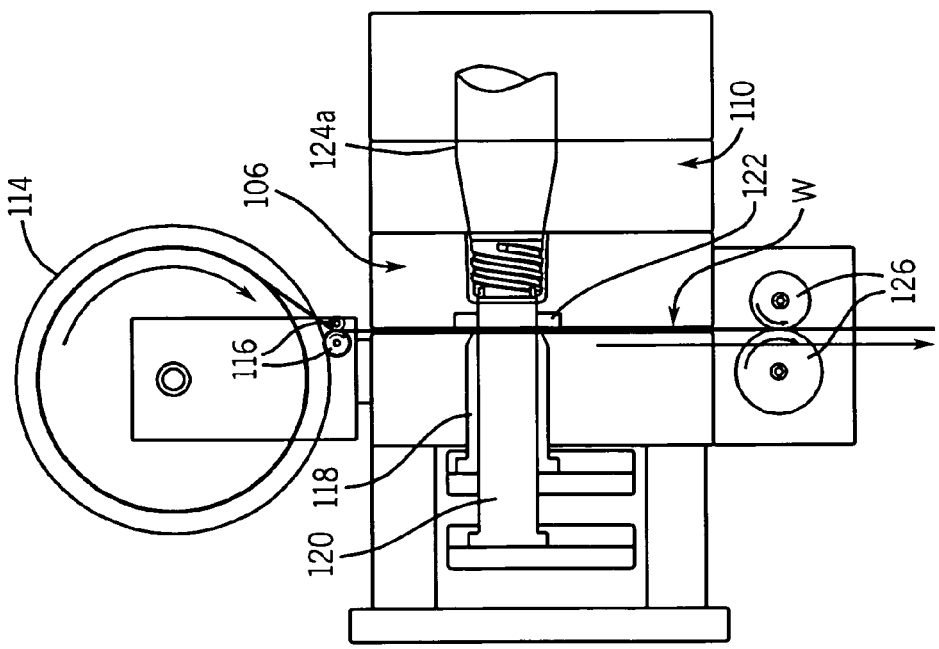

Referring now to FIG. 10C, the material for preparing the interior seal 18, e.g., a foil laminate in the form of a web "W" comprising, from top to bottom, (a) a layer of paper, (b) a layer of metallic foil, and (c) a layer of heat sealable adhesive, is supplied on a storage reel 114. The web "W" containing the material for forming the interior seal 18 is fed from the storage reel 114 through a set of guide rollers 116 into the mold zone 104 of the system 100. As indicated previously, the mold zone 104 comprises the molding unit 105, which comprises the first cavity half 106, the second cavity half 108, the first core half 110 and the second core half 112. The molding unit 105 can be an injection-molding unit. Injection-molding units are described in *Encyclopedia of Polymer Science and Engineering*, 2nd Edition, Vol. 8, John Wiley & Sons, Inc. (1987), pages 102-137, previously incorporated herein by reference. A retention sleeve 118 and a punch 120 are located in the mold zone 104, as is a die plate 122. The purpose of the retention sleeve 118 is to position and retain the web "W" against the die plate 122. The purpose of the punch 120 is to penetrate the web "W" and retain the interior seal 18 against a mold core, which will be described below. The purpose of the die 122 is to cooperate with the punch 120 to cut the web "W". Each core half contains a mold core. The mold core in the first core half 110 has the reference numeral 124a, and the mold core in the second core half 112 has the reference numeral 124b. Each cavity half contains a mold cavity. The mold cavity in the first cavity half 106 has the reference numeral 125a. The mold cavity in the second cavity half 108 has the reference numeral 125b. As the molding unit 105 is being closed, a set of advance rollers 126 is signaled to index the web "W" to the proper position relative to the mold zone 104.

Referring now to FIG. 10D, the retention sleeve 118 is urged in a first direction (left to right in FIG. 10D) to secure the material of the web "W" on the die plate 122. The punch 120 is advanced in the first direction to pierce the material of the web "W" and to secure the material of the web "W" on the end of the mold core 124a. As the molding unit 105 is closing, the material of the web "W" for forming the interior seal 18 is indexed through the punch 120 and the die plate 122 in the mold zone 104. Upon the closing of the molding unit 105 by joining the first core half 110 with the first cavity half 106, the punch 120 and die plate 122 are actuated, thereby enabling the punch 120 to cut the material of the web "W" for forming the interior seal 18 into the shape desired, e.g., a disk. The punch 120 continues to advance in the first direction, thereby placing and holding the interior seal 18 on the end of the mold core 124a until the termination of the first molding cycle. During the first molding cycle, the polymeric material for forming the cap 14 is introduced into the assembly formed by the first cavity half 106 and the first core half 110. In the case of injection molding, the polymeric material for forming the cap 14 is introduced by an injection step. The retention sleeve 118 and the punch 120 remain in position until the polymeric material for forming the cap 14 has cooled. As the polymeric material for forming the cap 14 is introduced into the assembly comprising the first cavity half 106 and the first core half 110, the heat of the molten polymeric material softens the bonding layer (the layer of heat sealable adhesive) on the material for preparing the interior seal 18 and allows the interior seal 18 to adhere to the polymeric material of the cap 14. In the case where a layer of heat sealable adhesive is not employed, the polymeric material that forms the cap 14 fixes the interior seal 18 into the desired position.

Figure 10F:
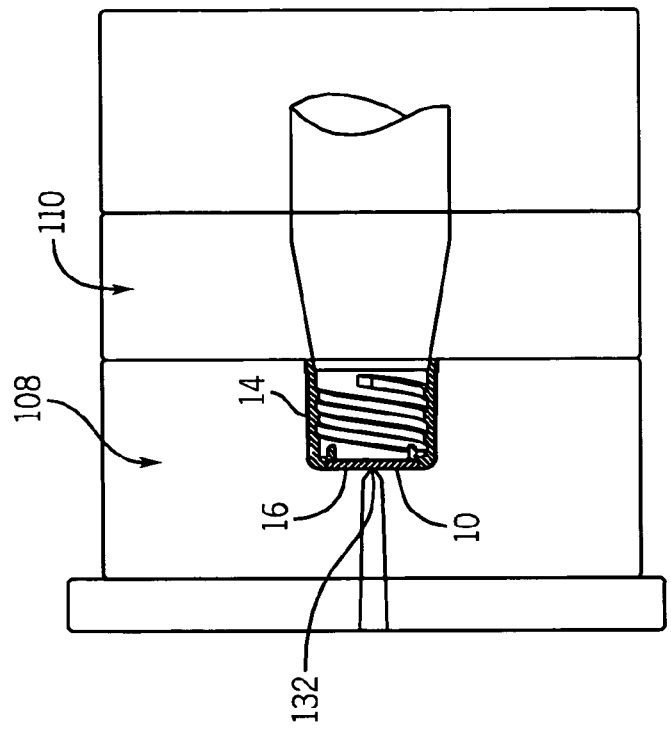
Figure 10E:
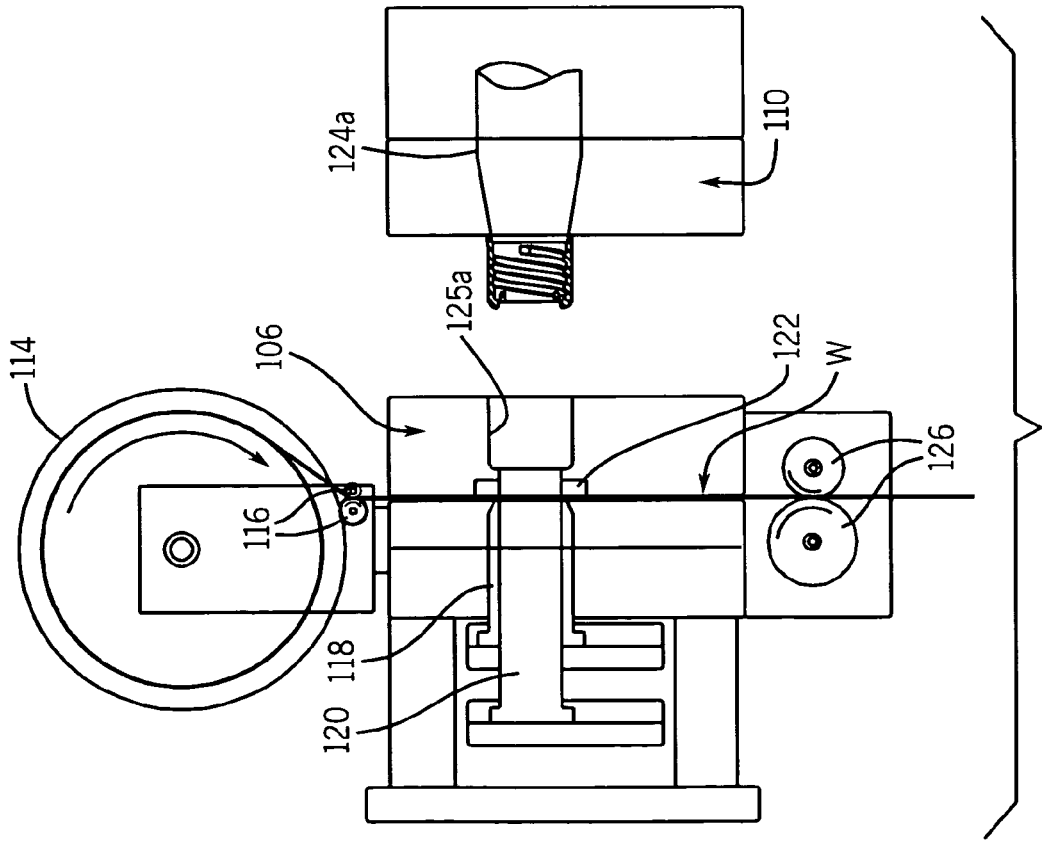

Referring now to FIG. 10E, when the assembly comprising the first cavity half 106 and the first core half 110 is opened, the retention sleeve 118 and the punch 120 are retracted in a second direction (right to left in FIG. 10E). The unfinished closure, i.e., the assembly comprising the cap 14 and the interior seal 18, remains on the mold core 124a. The interior seal 18 continues to adhere to the cap 14. Prior to the step shown in FIG. 10F, the first core half 110 and the second core half 112 are switched, e.g., by rotation, into position for introduction of the material into the assembly comprising the second cavity half 108 and the first core half 110 for preparing the exterior seal 16. Although the actual rotation step is not shown, the first core half 110 and the second core half 112 are rotated 180° so that the first core half 110 is in register with the second cavity half 108 and the second core half 112 is in register with the first cavity half 106. The rotational switch can be carried out either by a swing plate in the mold zone 104 or a rotary platen in the molding unit 105, or by an equivalent component. In alternative embodiments, core halves can be moved into proper position by movements other than rotational movements, e.g., by indexing.

Referring now to FIG. 10F, the first core half 110 is aligned with the second cavity half 108 and the assembly comprising the second cavity half 108 and the first core half 110 is closed. The material for forming the exterior seal 16 is then introduced into the assembly comprising the second cavity half 108 and the first core half 110, which contains the unfinished closure, so that the material for forming the exterior seal 16 flows over the web material that forms the interior seal 18. In the case of injection molding, the polymeric material for forming the exterior seal 16 is introduced by an injection step via a nozzle 132.

Figure 10G:
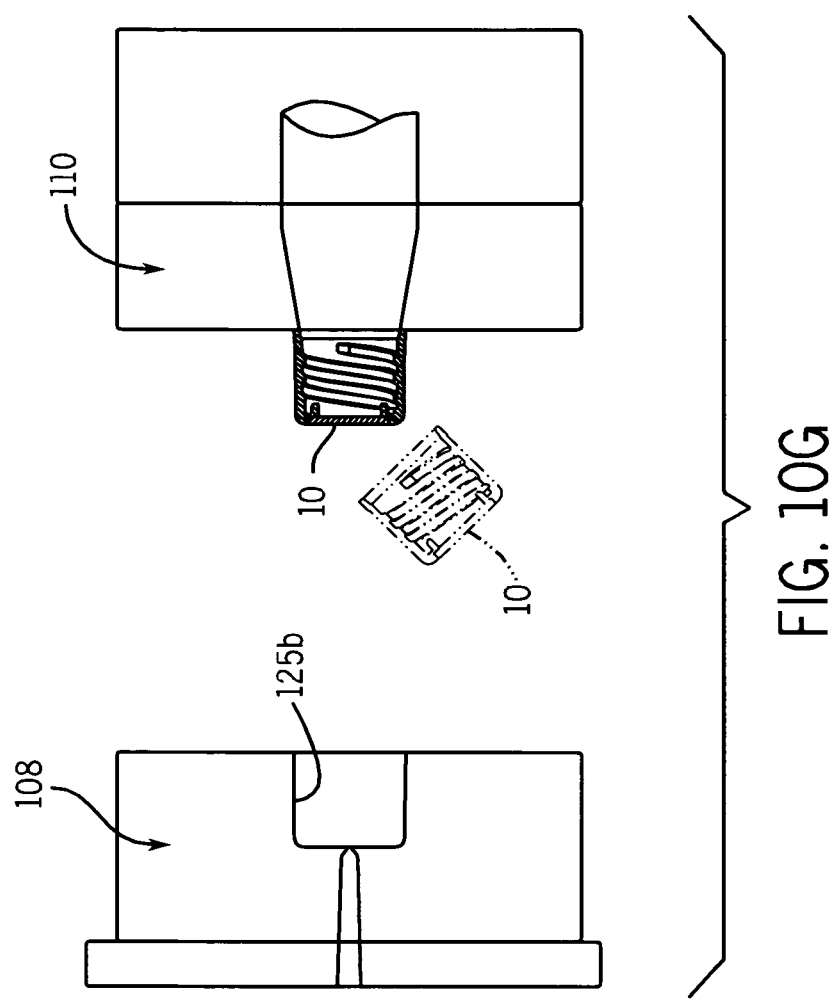

Referring now to FIG. 10G, after the material for forming the exterior seal 16 is cooled, the assembly comprising the second cavity half 108 and the first core half 110 is opened, and the closure 10 is removed from the mold core 124a and removed from the mold zone 104. A threaded closure is unscrewed from the mold core 124a, which is also threaded. The finished closure 10 drops onto a conveyor (not shown), from which it is transported into a shipping container (not shown).

The cavity halves 106 and 108 and the core halves 110 and 112 can be designed to provide the desired structures and shapes of the components of the closure 10. The at least one score line 36 or the at least one slit 38 can be formed by means of the molding step for preparing the exterior seal 16. The cavity halves 106 and 108 and the core halves 110 and 112 can be designed to provide the at least one score line 36 or the at least one slit 38 in the exterior seal 16. All of the design parameters of the molding unit 105 can be determined by one of ordinary skill in the art of injection molding without undue experimentation. See, for example, *Encyclopedia of Polymer Science and Engineering,* 2nd Edition, Vol. 8, John Wiley & Sons, Inc. (1987), pages 102-137, previously incorporated herein by reference.

The conditions of the molding cycles of this invention and other steps of the method for preparing the closure of this invention can be selected to provide adequate durations of time for introducing polymeric material into the molding unit 105, forming the components of the closure 10, and cooling the formed components of the closure 10. Furthermore, the foregoing conditions and other conditions of the molding process of this invention, e.g., mold release agents, can be determined by one of ordinary skill in the art of injection molding without undue experimentation. See, for example, *Encyclopedia of Polymer Science and Engineering,* 2nd Edition, Vol. 8, John Wiley & Sons, Inc. (1987), pages 102-137, previously incorporated herein by reference

OPERATION

In order to use the closure 10 of this invention, the closure 10 is screwed onto or fitted onto a container 12 containing a biological sample by means of the cap 14. During shipment, the biological sample will be sealed in the container 12, and little, if any, of the sample will seep out of, leak out of, or evaporate from the container 12. In order to obtain access to the biological sample in the container 12, a sampling device 50, such as, for example, a tip of a pipette, typically a disposable tip of a pipette, is inserted through the opening 22 in the top of the cap 14 with sufficient force to puncture the exterior seal 16 and rupture the interior seal 18. See FIG. 7. The biological sample or a portion thereof can be withdrawn by means of the sampling device 50. The sampling device 50 can subsequently be withdrawn from the container 12. In FIGS. 8 and 9, the exterior seal 16 has a slit 38 formed therein. Insertion of the disposable tip of a pipette through the slit 38 does not puncture the exterior seal 16, but merely passes through the slit 38, and then ruptures the interior seal 18. Thereupon, the biological sample or a portion thereof can be withdrawn by means of the sampling device 50. The sampling device 50 can subsequently be withdrawn from the container 12.

The disposable tip of a pipette can successfully puncture the exterior seal 16 and the interior seal 18 of the closure 10. The residue from the interior seal 18 does not clog the orifice of a disposable tip of a pipette, which can be determined by measuring the volume of fluid removed from the sample tube (e.g., 400 microliters). The disposable tip does not cause an overflow in the case of a sample tube containing eight milliliters of fluid. The volume replaced by a disposable tip is about one milliliter. Hanging drops are generally not observed on the disposable tip after the tip is removed from the sample tube. The pierced interior seal 18 appears to remove gross contamination as the tip of the pipette leaves the sample tube, although there may be some fluid coating the disposable tip.

The closure 10 and the container 12 of this invention can be used to prepare samples automatically. The closure 10 and the container 12 of this invention allow capped sample tubes, each containing a biological sample, to be placed on an analytical instrument without the necessity of removing the closures manually for obtaining access to biological samples.

The closure 10 and the container 12 of this invention can be used in automated sample preparation. The invention allows one to place a closed container 12 containing a biological sample to be placed on an instrument without having to remove the closure 10 for obtaining access to a sample. This invention can be used when large quantities of samples are tested, e.g., 600 samples per day.

When the interior seal 18 of the closure 10 is pierced, it is sufficiently frangible that it has a brittle fracture, with the result that it will not hug the tip of the pipette and form a vacuum. Therefore, an automated sample preparation system will withdraw the correct amount of biological sample. In addition, the interior seal 18 of the closure 10 will not produce so much drag that it will remove the disposable tip from the pipette. The interior seal 18 of the closure 10 is durable enough to withstand a fall from 46.9 inches (i.e., the elbow height of 95% of males) with the maximum quantity of biological sample contained in the container 12.

The parameters and failure modes relevant to the closure 10 of this invention include, but are not limited to, damage to disposable tips, failure to piece the closure, and suitable piercing force (as measured by an appropriate Instron® testing machine). For the purposes of this invention, the interior seal 18 of the closure 10 should neither be excessively strong nor excessively weak. The strength of the interior seal 18 of the closure 10 is determined by the force that will be exerted by the tip of a pipette. The force exerted by the tip of a pipette when the pipette ruptures the interior seal 18 of the closure 10 is preferably less than about three pounds, more preferably about one pound. The force exerted upon the tip of a pipette when the pipette is being retracted from the container 12 is preferably less than about one pound, in case the heat sealable adhesive of the interior seal 18 tends to cling excessively to the tip of the pipette. This feature takes on greater importance in the case of a disposable tip of a pipette, because excessive force exerted upon the disposable tip of a pipette during retraction thereof from a container could result in removal of the disposable tip from the pipette.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A closure for a container having a mouth, said closure comprising (a) a cap, said cap made of a polymeric material, (b) an interior seal having two major surfaces, said interior seal consisting essentially of a layer of brittle material, and (c) an exterior seal having two major surfaces, said exterior seal consisting essentially of an elastomeric material having a hardness ranging from about 30 Shore A to about 90 Shore A, said layer of brittle material having two major surfaces, a major surface of said layer of brittle material being in contact with a major surface of said exterior seal.

2. The closure of claim 1, wherein said cap comprises a substantially cylindrical body having a first opening and a second opening, said first opening capable of communicating with said mouth of said container, said second opening being sealed by said exterior seal, said interior seal being placed between said first opening and said exterior seal.

3. The closure of claim 2, wherein said first opening and said second opening are circular in shape.

4. The closure of claim 2, wherein said exterior seal is rupturable by a tip of a pipette and said interior seal is rupturable by a tip of a pipette.

5. The closure of claim 1, wherein said exterior seal has at least one score line scribed thereon.

6. The closure of claim 1, wherein said exterior seal has a plurality of score lines scribed thereon.

7. The closure of claim 1, wherein said exterior seal has at least one slit formed therein, through which at least one slit a tip of a pipette can pass.

8. The closure of claim 1, wherein said exterior seal has a plurality of slits formed therein, through which slits a tip of a pipette can pass.

9. The closure of claim 1, wherein said interior seal further comprises a layer of adhesive, said layer of brittle material interposed between said layer of adhesive and said exterior layer.

10. The closure of claim 1, wherein said polymeric material of said cap comprises a resilient polymeric material.

11. The closure of claim 1, wherein said polymeric material of said cap comprises polypropylene.

12. The closure of claim 1, wherein said layer of brittle material is a metallic foil.

13. An assembly comprising a container and the closure of claim 1.

14. The assembly of claim 13, wherein said container is made of a polymeric material.

15. The closure of claim 1, wherein said elastomeric material is selected from the group consisting of natural rubber, styrene-butadiene rubber, polyisoprene, silicone rubber, fluorosilicone rubber, and ethylene propylene rubber.

16. A closure for a container having a mouth, said closure comprising (a) a cap, said cap made of a polymeric material, (b) an interior seal having two major surfaces, said interior seal consisting essentially of a layer of brittle material, a layer of paper, a first layer of adhesive interposed between the layer of brittle material and the layer of paper, and (c) an exterior seal having two major surfaces, said exterior seal consisting essentially of an elastomeric material having a hardness ranging from about 30 Shore A to about 90 Shore A, said layer of paper having two major surfaces, a major surface of said layer of paper being in contact with a major surface of said exterior seal.

17. The closure of claim 16, wherein said cap comprises a substantially cylindrical body having a first opening and a second opening, said first opening capable of communicating with said mouth of said container, said second opening being sealed by said exterior seal, said interior seal being placed between said first opening and said exterior seal.

18. The closure of claim 17, wherein said first opening and said second opening are circular in shape.

19. The closure of claim 17, wherein said exterior seal is rupturable by a tip of a pipette and said interior seal is rupturable by a tip of a pipette.

20. The closure of claim 16, wherein said exterior seal has at least one score line scribed thereon.

21. The closure of claim 16, wherein said exterior seal has a plurality of score lines scribed thereon.

22. The closure of claim 16, wherein said exterior seal has at least one slit formed therein, through which at least one slit a tip of a pipette can pass.

23. The closure of claim 16, wherein said exterior seal has a plurality of slits formed therein, through which slits a tip of a pipette can pass.

24. The closure of claim 16, wherein said interior seal further comprises a second layer of adhesive, said layer of brittle material interposed between said second layer of adhesive and said first layer of adhesive.

25. The closure of claim 16, wherein said polymeric material of said cap comprises a resilient polymeric material.

26. The closure of claim 16, wherein said polymeric material of said cap comprises polypropylene.

27. The closure of claim 16, wherein said layer of brittle material is a metallic foil.

28. An assembly comprising a container and the closure of claim 16.

29. The assembly of claim 28, wherein said container is made of a polymeric material.

30. The closure of claim 16, wherein said elastomeric material is selected from the group consisting of natural rubber, styrene-butadiene rubber, polyisoprene, silicone rubber, fluorosilicone rubber, and ethylene propylene rubber.

* * * * *